United States Patent [19]

Anderson et al.

[11] Patent Number: 5,229,126
[45] Date of Patent: Jul. 20, 1993

[54] FLYING INSECT ATTRACTANT COMPOSITION

[75] Inventors: Douglas G. Anderson, Lakeville; Thomas D. Nelson, St. Paul, both of Minn.

[73] Assignee: Ecolab Inc., St. Paul, Minn.

[21] Appl. No.: 894,450

[22] Filed: Jun. 5, 1992

Related U.S. Application Data

[63] Continuation of Ser. No. 697,755, May 9, 1991, abandoned, which is a continuation of Ser. No. 367,371, Jun. 16, 1989, abandoned.

[51] Int. Cl.$^5$ ............................................. A01N 25/34
[52] U.S. Cl. .................................. 424/410; 424/405; 424/84
[58] Field of Search ........................ 427/405, 410, 84

[56] References Cited

U.S. PATENT DOCUMENTS

| | | | |
|---|---|---|---|
| 3,846,557 | 11/1974 | Mulla et al. | 426/1 |
| 3,993,072 | 11/1976 | Zaffaroni | 128/260 |
| 3,996,349 | 12/1976 | Mulla et al. | 424/84 |
| 4,160,335 | 7/1979 | Von Kohorn et al. | 43/131 |
| 4,202,129 | 5/1980 | Greenberg | 43/131 |
| 4,356,969 | 11/1982 | Obermayer et al. | 239/6 |
| 4,445,641 | 5/1984 | Baker et al. | 239/6 |
| 4,462,880 | 7/1984 | Hill et al. | 204/161 |
| 4,548,764 | 10/1985 | Munteanu et al. | 261/75 |
| 4,562,794 | 1/1986 | Speckman | 119/156 |
| 4,664,847 | 5/1987 | Williams | 252/522 |
| 4,735,798 | 4/1988 | Bernstein | 424/61 |
| 4,764,367 | 8/1988 | Wilson et al. | 424/84 |
| 4,855,133 | 8/1989 | Kamei et al. | 424/84 |
| 4,906,488 | 3/1990 | Pera | 426/573 |
| 4,947,578 | 8/1990 | Anderson et al. | 43/131 |

OTHER PUBLICATIONS

Reactions of the Pomace Fly—To Odorous Substances: Barrows, J. Expt. Zoology, vol. IV, 4, pp. 515–537.

"Chemical Attractants for the Adult House Fly" by A. W. A. Brown et al., vol. 5, No. 4, Journal of Economic Entomology, pp. 667–674 (Aug. 1961).

"An Improved Bait for Flies (Diptera: Muscidae, Caliphoridae)" by L. G. Pickens et al., vol. 10, No. 1: pp. 84–88, Journal of Medical Entomology, (Jan. 31, 1973).

"The Attraction of Diptera to Ammonia" by C. H. Richardson, vol. IX, Annals Entomological Society of America, pp. 408–413 (1916).

"Further Observations on the Effect of Certain Chemicals Upon Oviposition in the House Fly" by S. E. Crumb et al., vol. 14, No. 6, Journal of Economic Entomology, pp. 461–465 (Dec. 1921).

"A. Chemotropic Response of the House Fly (Musca domestica L.)" by C. H. Richardson, vol. 43, Science, pp. 613–616.

"Attractants for Synanthropic Flies: Ethanol as Attractant for Fannia canicularis and other Pest Flies in Poultry Ranches" by Hwang et al., vol. 4, No. 4, Journal of Chemical Ecology, pp. 463–470 (1978).

"The Designation of Chemicals in Terms of the Responses they Elicit from Insects" by V. G. Dethier et al., vol. 53, No. 1, The Journal of Economic Entomology, pp. 134–136 (Feb. 1960).

"Attractants for Synanthropic Flies: 3. Evaluation, Development, and Formulation of Attractive Baits Against Hippelates collusor" by M. S. Mulla et al., vol. 66, No. 5, Journal of Economic Entomology, pp. 1089–1094.

"Attractants for Synanthropic Flies: Chemical Attractant for Domestic Flies" by M. S. Mulla et al., vol 70, No. 5, Journal of Economic Entomology, pp. 644–648 (Oct. 1977).

"Controlled-Release Reservoir Systems for the Delivery of Insect Steroid Analogues Against Ticks (Acari: Ixodidae)", by H. Jaffe et al., vol. 23, No. 6, Journal of Medical Entomology, pp. 685–691 (Dec. 1986).

"Phenethyl Propionate, a Potent New Attractant for Japanese Beetles", by T. P. McGovern et al., vol. 63, Journal of Economic Entomology, pp. 1727–1729 (1970).

"Attraction of the Geman Cockroach to Cyclohexyl Alkanoates and n-Alkyl Cyclohexaneacetates" by R. Sugawara et al., Journal of Insect Physiology, vol. 21, pp. 957–964 (1975).

"Effects of Ring Unsaturation of the Activity of Propyl Cyclohexaneacetate as an Attractant for the German Cockroach" by R. Sugawara et al., Insect Biochemistry, vol. 7, pp. 483–485 (1977).

"Synthesis of the Pheromone of Oriental Fruit Moth, Grapholitha Molesta Busck—cis-8-dodecen-1-yl Acetate", by the Peking Institute of Zoology, *Hua Hsueh Hsueh Pao*, vol. 35, pp. 221-226 (1977).

"Improved Synthesis of Insect Sex Attractant cis-8-dodecen-1-ol Acetate" by G. Holan, vol. 9, *Tetrahedron Letters*, pp. 673-674 (1973).

"Synthesis and Biological Evaluation of Candidate Nonenyl Acetates as Melon Fly Ovipositional Attractants" by D. J. Voaden et al., vol. 32, *Journal of Agric. Food Chem.*, pp. 769-773 (1984).

"Attraction of Glischrochilus Quadrisignatus (Coleoptera: Nitidulidae) to Semiochemicals: Butyl Acetate and Propyl Propionate" by S. R. Alm et al., vol. 79, *Journal of Economic Entomology*, pp. 654-658 (1986).

"Detection of Volatile Neutral Components in Mulberry Leaves Harvested in Late Autumn" by Y. Iwanari, vol. 42, *Nippon Sanshigaku Zasshi*, pp. 403-405 (1973).

"On Ultrasound Absorption in Saturated Vapor of a Mixture of Ethyl Acetate and Ethyl Alcohol" by A. Mamadzhanov, *Chemical Abstracts*, 85:10518u, vol. 85 (1976).

"Food Substances Affirmed as Generally Recognized as Safe in Feed and Drinking Water of Animals; Ethyl Alcohol Containing Ethyl Acetate" by United States Food and Drug Administration, *Chemical Abstracts*, 95:218986, vol. 95 (1981).

"Determination of Ethyl Alcohol and Ethyl Acetate in Vinegar" by Zanin et al., *Chemical Abstracts*, 75618r, vol. 69 (1968).

"Volumetric Viscosity of the System Acetic Acid--Ethyl Acetate-Ethyl Alcohol-Water" by A. Normatov, *Chemical Abstracts*, 84:111810t, vol. 84 (1976).

"Thermodynamics of the Adsorption of Ethyl Alcohol-Ethyl Acetate and Ethyl Alcohol-Benzene Solutions on Silica Gel KSK-2" by S. A. Busev et al., *Chemical Abstracts*, 100-180615u, vol. 100 (1984).

*Primary Examiner*—Thurman K. Race
*Assistant Examiner*—Neil Levy
*Attorney, Agent, or Firm*—Merchant, Gould, Smith, Edell, Welter & Schmidt

[57] ABSTRACT

A formulated attractant for household flying pests and the optimal release rates have been found providing improved attractiveness when compared to prior art attractants including the use of fermented materials or hydrolyzed or other decomposed proteins. The attractant is pleasant and nontoxic to humans when used correctly, and is easily manufactured, stored and transported.

10 Claims, No Drawings

FLYING INSECT ATTRACTANT COMPOSITION

This is a continuation of application Ser. No. 07/697,755, filed May 9, 1991 abandoned, which is a continuation of application Ser. No. 07/367,371, filed Jun. 16, 1989, abandoned.

FIELD OF THE INVENTION

The invention relates to volatile insect attractant compounds for use in controlled release devices. The composition can be used in the human environment to attract flying insects over an extended period of time to insect traps or for other purposes. The preferred attractant is directed to the common household fly.

BACKGROUND OF THE INVENTION

Insects are the most numerous of all living organisms and nearly one million species constitute approximately 70 percent of all animal species. Of these, about 1 percent are considered significant pests. Overall, insects are known to attack humans and domestic animals; transmit human, animal, and plant diseases; destroy structures; and compete for available supplies of foods and fibers.

Of the insect pests, flying insect pests can be particularly troublesome. Such pests have been vectors for pathogenic organisms that can cause a variety of diseases in man and in domestic animals. Control of household flying insects for aesthetic, public health, and economic reasons are practiced all over the globe in human environments including houses, restaurants, food processing units, office buildings, and other locations in which humans or organic materials present an attractive environment for flying insect pests.

In the past, a number of pesticides have been identified that kill insect pests. Because of the toxicity of these chemicals to humans and to organisms other than those targeted by the pesticide, alternatives to routine pesticide use have been sought. Chemical attractants for pests are chemicals that can attract pests during a search for food, for oviposition (egg-laying) sites, or for mates. Many of these chemicals can be used as attractants to draw insect pests into mechanical traps or into poisoned baits for population control, for measurement of population densities and, for example, for selective or timed spray applications of the collected populations. In this way, insect attractants can be used for insect population control without pesticide or only with limited judicious pesticidal applications.

The science of insect pest attraction has a long history of development. The testing of attractants for attractancy has been performed in a variety of different ways. The testing methodology is rarely comparable. Further, published data on a chemical can be often contradictory. The earliest types of attractants were natural products related to hydrolyzed or decomposed protein materials or fermented plant materials. Natural attractants based on fermenting or decomposing natural products provide little opportunity to control release rates. Further, indoor use and outdoor use is severely limited by unacceptable odors and by rapid dehydration of the organic matter.

Attractants are typically relatively volatile organic compounds that can be released into the atmosphere. Each chemical attractant composition has a threshold level of attractancy at which point insects can detect the presence of the concentration of the attractant by olfactory receptors. Below such a threshold level, the chemicals tend not to be measurably different from nonattractive compositions in affecting insect behavior. Each attractant has an effective concentration range which is dependent upon its release rate into the environment within which the attractants are effective to alter the behavior of insects in a way that attracts the insects to the attractant composition. Above the effective concentration range for each attractant, the attractancy of the composition is typically lessened, and often at higher release rates, the resulting concentrations of the material in the atmosphere act as effective repellents. A few chemical attractants have been introduced for commercial use. These attractants are typically phermones which are chemicals released by insects for the purpose of attracting mates. Such compounds are used at very low levels and are typically dispensed into the environment on a carrier such as porous plastic or a natural product such as corncob grits.

A substantial need exists for an attractant material to be used in the human environment to attract insects, particularly flying insect pests, which is effective, is non-offensive to humans, and is nontoxic when used correctly.

SUMMARY OF THE INVENTION

We have found for the first time that flying insect pests can economically and effectively be attracted by the release of ethanol at a rate of at least about 0.02 gms/hr into the human environment. We have further found that a combination of a major proportion of an ethanol attractant and an effective amount of a volatile $C_{1-5}$ alcohol ester of a $C_{1-3}$ carboxylic acid is a more effective flying insect attractant than ethanol alone. The liquid material has a very pleasant, mild ethanolic odor. At the release rates of ethanol and volatile ester used in attracting flying insect pests, the material provides a barely detectable, or low level of a background, mild, somewhat fruity odor. The attractant material is most commonly dispensed from a container having a controlled release mechanism used in conjunction with any type of insect trap, thus removing the flying insects from the human environment.

The attractants of the invention can be released by a variety of release mechanisms or from a variety of release compositions. The attractants can be used to lure flying insects to mechanical or electrical traps, toxic food baits, or oviposition baits, to a locale which can be sprayed intermittently when large populations of insects are attracted by the attractant, to areas treated with pesticides having extended lifetime, or can be used for the purpose of monitoring the magnitude and changes in flying insect populations. The human environment discussed in this application refers to environments within a closed structure in which humans work, reside or recreate. Such structures include homes, apartments, offices, factories, restaurants, food processing or preparatory areas, or any other areas where humans or their activities attract flying insect pests.

DETAILED DISCUSSION

Household flying insect pests have a wide distribution. Typical flying insect pests that are attracted to the compositions of the invention are flies belonging to the order Diptera and include flies of such families are Phoridae, Psychodidae, Fungivordidae Chloropidae, Calliphoridae, Sarcophagidae, Anthomyiidae, Muscidae, and Drosophilidae. The primary flying insect pests attracted to the preferred attractants of this invention are flies of the Muscidae family and particularly *Musca domestica*, the common house fly.

Ethanol is a clear, nonstaining liquid that has a mild, pleasant background odor. At useful release rates and at concentrations in the air useful in flying insect attractants, the ethanol component is effective and non-toxic to humans. Ethanol and, in particular, denatured ethanol can be toxic only if the attractant composition is misused by ingestion of the liquid material.

The volatile ester co-attractants used with the ethanol in the compositions of this invention are typically used at low concentrations in the ethanol and add little to the odor, toxicity or appearance of the attractant compositions. However, each of these volatile low-molecular weight ester compositions has a pleasant aroma, while some have a pleasant fruity aroma.

The volatile ester compound useful in combination with ethanol in the liquid attractant composition of the invention are esters of the formula:

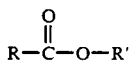

wherein R is a $C_{1-3}$ alkyl group and R' is a $C_{1-6}$ branched or unbranched alkyl group. These esters are made using common organic preparatory techniques. Preparatory procedures for the manufacture of such esters are well known in the art. The volatile esters can be made from lower alcohols and lower carboxylic acids by common esterification techniques from lower alcohols and lower carboxylic acids and their reactive analogues.

Lower alcohols useful in the manufacture of the volatile ester co-attractants of the invention include methyl alcohol, ethyl alcohol, n-propyl alcohol, isopropyl alcohol, n-butyl alcohol, isobutyl alcohol, tertiary butyl alcohol, n-amyl alcohol, isoamyl alcohol, tertiary amyl alcohol, n-hexyl alcohol, and mixtures thereof, etc. Carboxylic acids useful in manufacturing the ester attractant of the invention include acetic acid, propionic acid, butyric acid, mixtures thereof, and others. The associated reactive analogs can be used, for example, the acid chloride or acid anhydride.

The preferred volatile ester is a volatile compound at ambient or room temperature and pressure. The volatile ester should have a vapor pressure comparable to ethanol with which the ester co-attractant is used in the compositions of the invention. Accordingly, the volatile ester co-attractants of the invention should have a vapor pressure of at least about 30 mm Hg, and a preferred vapor pressure of about 40 to 70 mm Hg. The matching of the ester vapor pressure to the vapor pressure of ethanol ensures that the released attractant will have a uniform concentration of ethanol and volatile ester.

The volatile ester attractant composition of the invention can be used with ethanol in a proportion of about 0.05 to 5 parts of the volatile ester co-attractant for each one hundred parts of ethanol, preferably about 0.1 to 1 parts volatile attractant is used for each one hundred parts of ethanol, and preferably for reasons of effective attractant properties and economy, the volatile ester is used at a concentration of about 0.2 to 0.8 parts of volatile ester per each one hundred parts of ethanol.

The preferred volatile ester for use in this invention is a lower alcohol acetate ester such as n-amyl acetate, isoamyl acetate, isobutyl acetate, n-propyl acetate, ethyl acetate or mixtures thereof.

In use, the attractant composition can be introduced into the human environment at a rate of about 0.02–0.2 gm/hour, preferably 0.03 to 0.1 gm/hour, most preferably 0.04 to 0.08 gm/hr. Such release rates provide an effective concentration of the attractant in the region to which the flying pests are to be attracted. There is no upper level of the concentration of the attractant composition of the invention except that ethanol and the volatile ester can saturate the atmosphere at some concentration depending on temperature, humidity, and the recycle rate of the atmosphere. Such concentrations are much greater than is required for effective pest attraction. Since the ethanol ingredient is moderately flammable, concentrations of the attractant in the air should be maintained below the lower explosive limit of ethanol at the use temperature.

If desired, a nonvolatile liquid diluent can be used in which the ethanol and the co-attractants can be dissolved or dispersed. Preferred nonvolatile diluents must be inactive with respect to flying pest attractancy, and release the ethanol-volatile ester co-attractants into the atmosphere while remaining substantially unvolatilized. The insect attractants of the invention are used neat, that is, without diluent. The effects of the use of a variety of compositions on attracting, when used with the attractant of the invention, is unpredictable.

The ethanol volatile ester composition can be used in the form of an inert solid that is formulated to release the composition at a constant or near constant rate.

The volatile attractant composition of the present invention can be used in combination with a particulate solid carrier, such as a cellulosic material, sugars, silicates, clays, corncob grits, and similar particulate supports. The liquid mixture can then be sprayed on the solid particulate carrier. The preferred support has little flying insect repellency or attractancy.

The volatile attractant composition of the invention can be used in combination with ingredients that form a solid mass. The solid mass can be formed by taking particulate with an effective concentration of the attractant composition of the invention and compacting the material into a large mass. Alternatively, the attractant composition of the invention can be combined with ingredients that can be placed in a form that solidifies into the attractant solid. Such attractant solids release the attractant composition of the invention either by diffusion of the attractant through the solid into the air, or by releasing the attractant at the surface of the solid as the solid material is volatilized, decomposed, or eroded.

Included with the concept of a solid material, including the attractant compositions of the invention, are small particles of encapsulated volatile attractant within a permeable polymeric enclosure. Such encapsulated materials are released by diffusion or permeation of the volatile material through the polymer envelope or encapsulate. The rate of diffusion is primarily dependent on the nature of the polymeric envelope, temperature, and humidity.

PREFERRED RELEASE MEANS

The liquid insect attractant compositions of the invention can be released from a system comprising a container or reservoir for the liquid attractant having means to release the attractant vapor. The container can have an aperture closed by a membrane that can release the attractant vapor. The preferred membrane is a semi-permeable membrane. By semi-permeable membrane, we mean a membrane that retains liquid attractant and releases only vapor. The release rate of the volatile liquid attractant is controlled by the dimensions of the container, the dimensions of the aperture and the rate that the volatile attractant material can pass from the container (e.g.) through the semi-permeable membrane.

A variety of membranes can be used in the release means of the invention. Membranes are selected to ensure that the release means of the invention can dispense at least about 0.02 grams of the attractant per hour. Preferably, the membrane can release 0.03 to 0.2 grams of the attractant per hour. Typically such membranes comprise sheet-like polymeric materials that can release the attractant at the desired rate. Alternatively, the membranes can be manufactured to inherently contain pores of sufficient size to release the liquid attractant materials at the effective release rates. Polymeric materials useful in forming such releasing membranes are known in the art and include polyethylene, polypropylene, nylon, polytetrafloroethylene, polychlorotrifloroethylene, polystyrene, polyester, polyvinyl chloride, etc.

Containers for the volatile attractant materials of the invention can be made from a variety of materials such as steel, aluminum, engineering polymers such as polyester, polypropylene, high density polyethylene, etc. The container can be formed and assembled using known technology.

The container can be formed with an aperture closed by the vapor releasing, semi-permeable membrane. Such aperture is sized to release the attractant at the desired rate. Accordingly, for the attractants of this invention, the aperture is typically from about 0.1 to 5 centimeters in diameter, preferably about 0.2 to 2 centimeters. The attractant composition can be used in a trap or other flying pest holding apparatus which is designed to have a lifetime in its use locus from about 1 day up to 6 months. Accordingly, the container must have a capacity for approximately 0.5 to 4500 gms of attractant in order to provide such a lifetime at the release rates set for the attractant. Preferably, to have a lifetime of approximately 1 to 3 months in the human environment, the container has a capacity of about 15 to 2200 gms.

The release rate of the vapor attractant through the membrane can be reduced due to the consumption of substantial portions of the liquid attractant. Since the passage of the attractant vapor from the liquid level to the interior membrane surface is diffusion controlled, as the liquid level drops, the rate at which the vapor contacts the membrane can also be reduced. Accordingly, the container can be designed with a shape or other means designed to obtain a nearly constant liquid level within the container or vapor concentration at the interior membrane surface.

The container can be filled with a porous material that holds the liquid attractant material. An absorbent can be selected which is saturated with the attractant and fills substantially entirely the interior of the container. The surface of the absorbent is positioned directly adjacent to, but not in contact with, the release membrane, thus, presenting the membrane with the liquid attractant at a constant distance. Alternatively, the interior of the container can be configured with a wick mechanism which is a typically fibrous web. Such a web is immersed in the liquid attractant which is brought by the wicking action substantially to the release membrane surface. Such a web can act as a small passageway from the liquid bulk to the membrane. The web can be made of a woven or nonwoven fibrous material, such as cellulose, polyester, nylon, rayon, etc. The web can take a variety of forms. The web can be a free-standing cylinder extending from the bottom of the container to the membrane surface, or can be a mass of porous woven or nonwoven material attached to the sidewall of the container extending from the bottom of the liquid mass to the membrane surface. The purpose of the conduit is to provide a porous passageway directing the liquid from the bulk liquid to the interior surface of the membrane.

Alternatively, the volatile attractant compositions of the invention can be dispensed from release means comprising a container formed entirely from nonporous flexible polymeric sheet materials which do not permit liquid flow of the attractant but provide molecular diffusion of the attractant vapor through the flexible polymeric sheet. Such dispensing means can be manufactured by extruding continuous cylinders or envelopes of the polymeric material, filling the material with attractant and sealing the polymeric container forming a reservoir within the polymeric material filled with the attractant. The volume of the reservoir can be adjusted to provide a lifetime of the dispensing means in the environment from 1 day to 6 months depending upon the release rates or the molecular diffusion rate of the attractant through the polymer layer.

Alternatively, the release means of the invention can be made by taking a strip of a deformable impermeable material and pressing into the surface of the deformable material, a recessed volume, placing the liquid attractant material into the recessed area and covering the recessed area with the second strip material, trapping the attractant within the volume. The overlying strip material can be a barrier to the liquid but permeable to molecular diffusion of the attractant vapor.

In order to produce a release means useful in the environment, the release means must be fabricated such that it does not release attractant into the environment until needed. Accordingly, the permeable surfaces of any of the release means of the invention must be covered by a barrier material holding attractant within the container until the barrier is removed releasing the vapor. The barrier can be removed when the filled release means is placed into a locus for use. If the deformed reservoir portion is formed from a barrier material and the covering layer is formed from a permeable material, a barrier layer can be placed over the permeable layer which is removed prior to use. If the device is manufactured entirely from permeable material, the entire device must be enclosed within a barrier film envelope. Alternatively, the release means can be shipped empty and can be filled when placed in service.

TABLE I

Threshold Attractancy Determination for Ethanol

| ETHANOL RELEASE RATE (g/hr) | M. domestica[1] ATTRACTANCY |
| --- | --- |
| 0.097 | + |
| 0.093 | + |
| 0.083 | + |
| 0.068 | + |
| 0.060 | + |
| 0.052 | + |
| 0.041 | + |
| 0.027 | + |

TABLE I-continued

| Threshold Attractancy Determination for Ethanol | |
|---|---|
| ETHANOL RELEASE RATE (g/hr) | M. domestica[1] ATTRACTANCY |
| 0.024 | + |
| 0.019 | + |
| 0.019 | − |
| 0.009 | − |

*M. domestica* attractancy determined by replicated, multiple site testing in comparison to a water control. Attractancy (+) indicates the number of flies caught/30 minutes at the ethanol release rate shown significantly exceeds the number of flies caught/30 minutes with water at the same site. Testing was performed with 13-14 day old flies present at an average density of 0.1 fly/ft$^3$ at 75°-85° F. with 30-60 v/v % R.H.

TABLE II

| ATTRACTANT COMPARISON SUMMARY | | |
|---|---|---|
| | FLIES CAUGHT/30 MINUTES[2] | |
| ATTRACTANT[1] | MEAN | MEDIAN |
| Water | 2.68$^a$ | 2.0$^a$ |
| Ethanol | 5.08$^a$ | 4.0$^a$ |
| Ethanol (.995) + Amyl Acetate (.005) | 8.14$^a$ | 6.5$^a$ |
| Methanol | 2.50$^b$ | 2.0$^b$ |
| Methanol (.995) + Amyl Acetate (.005) | 2.83$^b$ | 2.0$^b$ |

[1] Attractants released at a rate of 0.024–0.156 g/hr.
[2] *M. domestica* caught in replicated, multiple site comparative tests.
$^a$ n = 48
$^b$ n = 12

TABLE III

| QUANTITATIVE PAIRED ATTRACTANT COMPARISON | | |
|---|---|---|
| ATTRACTANT PAIR | PERFORMANCE[1] | MEAN DIFFERENCE[2] FLIES CAUGHT/ 30 MINUTES |
| Ethanol vs. Water | +0.66 ○0.17 −0.17 | 2.40 |
| Ethanol (.995) + Amyl Acetate (.005) vs. Ethanol | +0.67 ○0.10 −0.23 | 3.06 |
| Ethanol (.995) + Amyl Acetate (.005) vs. Water | +0.88 ○0.08 −0.04 | 5.46 |

[1] Forty-eight replicates comparing the attractancy of water, ethanol and ethanol (.995) + amyl acetate (.005) were performed. The +, ○, and − indicate the proportion of those comparisons in which the first attractant caught more, equal and less flies, respectively, than the second attractant.
[2] Difference of mean catch of second attractant subtracted from mean catch of first attractant. Paired t-test analyses indicates that all attractant pairs are significantly different, with P < 0.001 for all pairs. In practical terms, these data indicate that the chances these results would be obtained by random chance with attractants with similar attractancy are less than 1 in 1000. Stated more directly, ethanol (.995) + amyl acetate (.005) is a statistically significantly more effective attractant than ethanol, which is a statistically significantly more effective attractant than water.

The data in Tables I through III show that ethanol, released alone, is an attractant for flies and has a threshold attractancy at a release rate of about 0.02 grams of ethanol per hour. Table II shows a cooperation between ethanol and the ester (amyl acetate) in the tests. At a concentration of 0.05 v/v % of amyl acetate in ethanol, the blended attractant is a significantly better attractant than water, ethanol alone, methanol alone, and a methanol/amyl acetate mixture. Table III again shows the superiority of an ethanol and 0.05 v/v % amyl acetate blended attractant over an ethanol attractant. Furthermore, the data shows the superiority of an ethanol attractant over water.

The specification, data, and examples, set forth above, provide a basis for understanding the invention and certain embodiments of the invention. However, the invention can take a variety of embodiments without departing from the spirit or scope of the invention. Accordingly, the invention resides in the claims hereinafter appended.

What is claimed is:

1. A controlled release system for an attractant for insect pests of the order Diptera, which system releases a pleasant and nontoxic attractant vapor into a human environment, said system comprising:
    (a) an attractant which consists essentially of ethanol and about 0.05 to 5 parts, per each one hundred parts of ethanol, of a volatile ester selected from the group consisting of n-amyl acetate, isoamyl acetate, tertiary amyl acetate, or mixtures thereof, in the absence of diluent; and
    (b) a container holding said attractant; wherein said container releases said attractant at a rate of about 0.02 to 0.1 gm/hr into the human environment.

2. The system of claim 1 wherein the ester has a vapor pressure of at least 30 mm Hg.

3. The system of claim 1 wherein the ester has a vapor pressure of at least about 40 to 70 mm Hg.

4. A controlled release system for an attractant for flying insect pests belonging to the order Diptera, which is non-aqueous and nontoxic in a human environment, said system comprising:
    (a) an attractant which consists essentially of ethanol and about 0.1 to 1 part, per each one hundred parts of ethanol, of a volatile ester selected from the group consisting of n-amyl acetate, isoamyl acetate, tertiary amyl acetate, in the absence of diluent, or mixtures thereof and having a vapor pressure of about 40 to 70 mm Hg; and
    (b) a container holding said attractant; wherein the container releases said attractant at a rate of about 0.03 to 0.1 gm/hr into the human environment.

5. A controlled release system for an attractant for *Musca domestica*, having a vapor nontoxic at use concentrations, said system comprising:
    (a) an attractant consisting essentially of ethanol and about 0.05 to 5 parts, per each one hundred parts of ethanol, of a volatile acetic acid ester comprising n-amyl acetate, isoamyl acetate, tertiary amyl acetate, or mixtures thereof; and
    (b) a container holding said attractant; wherein said container releases said attractant at a rate of about 0.03 to 0.2 gm/hr into the human environment.

6. The system of claim 5 wherein the ester has a vapor pressure of at least 30 mm Hg.

7. The method of claim 6 wherein the ester is present at a concentration of about 0.1 to 1 part of the ester per each one hundred parts of ethanol.

8. The method of claim 6 wherein the release rate of the attractant comprises about 0.03 to 0.1 gm/hr in the attractant.

9. The method of claim 7 wherein the vapor contains both ethanol and the volatile ester at a ratio that is substantially constant during the release of the liquid attractant.

10. The method of claim 7 wherein the release rate of the attractant remains effective to attract insects while the container holds liquid attractant.

* * * * *